US00PP18772P2

(12) United States Plant Patent
Bradford

(10) Patent No.: US PP18,772 P2
(45) Date of Patent: Apr. 29, 2008

(54) NECTARINE TREE NAMED 'KAY DIAMOND V'

(50) Latin Name: *Prunus Persica*
Varietal Denomination: Kay Diamond V

(76) Inventor: Lowell Glen Bradford, 10237 E. Mariposa Way, Le Grand, CA (US) 95333

( * ) Notice: Subject to any disclaimer, the term of this patent is extended or adjusted under 35 U.S.C. 154(b) by 0 days.

(21) Appl. No.: 11/637,907

(22) Filed: Dec. 13, 2006

(51) Int. Cl.
*A01H 5/00* (2006.01)

(52) U.S. Cl. ..... Plt./190
(58) Field of Classification Search ..... Plt./190
See application file for complete search history.

(56) References Cited

U.S. PATENT DOCUMENTS

PP15,845 P2 * 7/2005 Bradford

* cited by examiner

*Primary Examiner*—Kent Bell

(57) ABSTRACT

The present invention relates to a new and distinct variety of nectarine tree, *Prunus persica*, broadly characterized by a medium size, vigorous, hardy, self-fertile, productive and regular bearing tree. The fruit matures under the ecological conditions described in the early part of June, with first picking on Jun. 2, 2006. The fruit is uniformly large in size, acidic and sweet in flavor, globose in shape, clingstone in type, firm in texture, yellow in flesh color, and full red in skin color.

1 Drawing Sheet

Botanical classification: *Prunus persica.*
Variety denomination: 'KAY DIAMOND V'.

BACKGROUND OF THE VARIETY

In a continuing effort to improve the quality of shipping fruits, I, the inventor, typically hybridize a large number of peach, nectarine, plum, apricot, and cherry seedlings each year. I also grow a lesser number of open pollinated seeds of each of these fruits, usually to capture recessive traits. The present invention relates to a new and distinct variety of nectarine tree, which has been denominated varietally as 'KAY DIAMOND V'.

During the spring of 1996 I gathered fruit from several different unnamed seedlings in my experimental orchard located near Le Grand, Calif., in Merced County (San Joaquin Valley). One particular group of nectarines was early in maturing, yellow in flesh color, and aptly designated as "EYN (OP)". I used embryo rescue techniques to germinate the seeds from this fruit, grew them as seedlings on their own root in my greenhouse, and upon reaching dormancy transplanted them to a cultivated area in the experimental orchard described above. During the fruit evaluation season of 2000 I selected the present variety as a single tree from this group of "EYN (OP)" described above. Subsequent to origination of the present variety of nectarine tree, I asexually reproduced it by budding and grafting in the experimental orchard described above, and such reproduction of plant and fruit characteristics were true to the original plant in all respects. The reproduction of the variety included the use of 'Nemaguard' rootstock (unpatented) upon which the present variety was compatible and true to type.

The present variety is most similar to 'Rose Bright' (U.S. Plant Pat. No. 15,845) nectarine by producing nectarines that are very firm in texture, clingstone in type, yellow in flesh color, and full red in skin color, but is distinguished therefrom by requiring more chilling hours and by producing fruit that is larger in size, has more freckles on the apex, and matures about five days earlier.

SUMMARY OF VARIETY

In summary, the present variety is characterized by a medium size, vigorous, hardy, self-fertile, productive and regular bearing tree. The fruit matures under the ecological conditions described in the early part of June, with first picking on Jun. 2, 2006. The fruit is uniformly large in size, acidic and sweet in flavor, globose in shape, clingstone in type, firm in texture, yellow in flesh color, and full red in skin color.

DRAWING

The accompanying photograph consists of four whole fruits positioned to display the characteristics of the skin color and form, one fruit divided transversely to the suture plane to reveal the flesh and stone, a freshly cleaned stone, various leaves, and a typical tip shoot.

POMOLOGICAL CHARACTERISTICS

Referring now more specifically to the pomological characteristics of this new and distinct variety of nectarine tree, the following has been observed under the ecological conditions prevailing near Le Grand, Merced County (San Joaquin Valley), Calif., and was developed at the state of firm ripe on Jun. 6, 2006, on the original tree during its tenth growing season. All major color code designations are by reference to the Inter-Society Colour Council, National Bureau of Standards. Common color names are also used occasionally.

TREE

Size: Medium, reaching and maintaining a height of 10' [3.05 m.] and a spread of 8' [2.44 m.] after ten growing seasons utilizing typical dormant pruning.

Vigor: Vigorous, responding typically to irrigation and fertilization. The variety grows about 3' [0.91 m.] of surplus top-growth during the spring and summer. The plant should be grown on a standard commercial rootstock for production purposes.
Growth: Upright and dense.
Form: Vase formed.
Hardiness: Hardy with respect to central California winters.
Heat tolerance: Observed to perform adequately in typical central California climatic conditions, which typically include extended periods of heat.
Drought tolerance: Variety is developed for commercial orchards and requires regular irrigation.
Production: Productive, thinning necessary.
Fertility: Self-fertile.
Bearing: Regular bearer with no alternate bearing yet observed.
Approximate chilling requirement: 700 hours.
Trunk:
*Size.*—Medium, reaching a maximum diameter of 5" [127 mm.] after the tenth growing season.
*Texture.*—Shaggy.
*Bark color.*—A Moderate olive brown [95. m.OlBr] and Dark reddish brown [44. d.rBr] variegation with Light yellowish brown [76. l.yBr] crevices present.
*Lenticels.*—Approximate Number Per Square Inch: 5. Color: Moderate orange yellow [71. m.OY]. Typical Size: ⅛" [3.2 mm.] to 7⁄16" [11.1 mm.]. Shape: Eye-shaped to elongated.
Branches:
*Size.*—Diameter of limb is 2½" [64 mm.] measured 12" above the crotch, 1¼" [32 mm.] measured 12" above the first fork.
*Texture.*—Smooth on first and second year wood, increasing roughness with age.
*Color.*—1st Year Wood Topside: Grayish red [19. gy.R]. 1st Year Wood Underside: Brilliant yellow green [116. brill.YG]. Older Wood: Deep yellowish brown [75. deep yBr].
*Lenticels.*—Number Per Square Inch: More than 50 on second year wood. Color: Light orange yellow [70. l.OY]. Typical size: 1⁄64" [0.4 mm.] to 3⁄32" [2.4 mm.] on second year wood. Shape: Elongated.
Leaves:
*Size.*—Large. Average Length: 6" [152 mm.]. Average Width: 1 9⁄16" [40 mm.].
*Arrangement.*—Alternate.
*Thickness.*—Medium.
*Form.*—Elliptical.
*Apex.*—Acuminate.
*Base.*—Acute, with a base angle of 70 to 80 degrees.
*Surface.*—Smooth.
*Color.*—Dorsal Surface: Moderate olive green [125. m.OlG]. Ventral Surface: Moderate yellow green [120. m.YG].
*Margin.*—Finely serrate.
*Venation.*—Pinnately net veined.
*Vein color.*—Light yellow green [119. l.YG].
*Petiole.*—Average Length: ½" [12.7 mm.]. Average Thickness: 1⁄16" [1.6 mm.]. Color: Brilliant yellow green [116. brill. YG].
*Stipules.*—Number: Usually 2 per leaf, up to 6 per growing tip. Average Length: ¼" [6.4 mm.]. Color: Very yellow green [115. v.YG] becoming Strong yellowish brown [74. s.yBr] with maturity.
*Glands.*—Number: 2 to 4 per leaf. Position: Alternately positioned on petiole and base of blade. Size: Medium. Form: Globose. Color: Strong yellow green [117. s.YG] becoming Moderate reddish brown [43. m.rBr] with age.
*Leaf buds.*—Pointed, medium in size.
Flower buds:
*Hardiness.*—Hardy, with respect to central California winters.
*Diameter.*—Typically ⅜" [9.5 mm.] 1 week before bloom.
*Length.*—Typically 9⁄16" [14.3 mm.] 1 week before bloom.
*Form.*—Not appressed.
*Surface.*—Pubescent.
*Color.*—Moderate purplish pink [250. m.pPk].
Flowers: Perfect, complete, perigynous, usually a single pistil, typically thirty or more stamens, five sepal and petal locations alternately positioned.
*Type.*—Showy, large.
*Average flower diameter.*—1 13⁄16" [46.0 mm.].
*Number of petals.*—Usually five, some extra petal fragments and double blossoms observed.
*Petal shape.*—Circular to oval.
*Petal margin.*—Somewhat wavy.
*Average petal diameter.*—¾" [19.1 mm.].
*Average petal length.*—13⁄16" [20.6 mm.].
*Petal apex.*—Rounded.
*Petal base.*—Rounded to somewhat truncate.
*Petal color.*—Pale pink [7. p.Pk] toward the apex, Light pink [4. l.Pk] toward the base.
*Anther color.*—Dark red [16. d.R] over a Light yellow [86. l.Y] center at bloom onset.
*Stigma color.*—Light greenish yellow [101. l.gY].
*Sepal color.*—Dark purplish red [259. d.pR].
*Sepal length.*—¼" [6.4 mm.].
*Sepal width.*—3⁄16" [4.8 mm.].
*Average pistil length.*—¾" [19.1 mm.].
*Average stamen length.*—⅝" [15.9 mm.].
*Fragrance.*—Moderate.
*Blooming period.*—Late, ten days after 'Rose Bright' (U.S. Plant Pat. No. 15,845) nectarine.
*Onset of bloom.*—One percent on Mar. 5, 2006.
*Date of full bloom.*—Mar. 15, 2006.
*Duration of bloom.*—One to two weeks, dependent on ambient temperature.
*Number per cluster.*—1 to 3 with single flowers most common.

FRUIT

Maturity when described: Firm ripe, Jun. 6, 2006.
Date of first picking: Jun. 2, 2006.
Date of last picking: Jun. 12, 2006.
Size: Uniform, large.
*Average diameter axially.*—3" [76.2 mm.].
*Average diameter across suture plane.*—3¼" [82.6 mm.].
*Average diameter across cheek plane.*—3⅛" [79.4 mm.].
*Typical weight.*—8.0 ounces [227 grams].
Form: Uniform, somewhat asymmetrical.
*Longitudinal section form.*—Elliptical to oblate.
*Axial view.*—Round.
Suture: A shallow groove extending from the base, along the side, and extending past the pistil point in a slight depression, sharper toward the apex.
Venation surface: Rounded, lipped toward the apex.
Lips: Somewhat unequal.

Cavity: Flaring, circular to elongated in the suture plane, suture showing on one side, Light yellow [86. l.Y] stem markings typical.
*Depth.*—9/16" [14.3 mm.].
*Breadth.*—1 1/16" [27 mm.].
Base: Truncate.
Apex: Rounded, somewhat cordate if viewed parallel to the suture.
*Pistil point.*—Apical, short, usually depressed within the suture.
Stem: Medium.
*Average length.*—3/8" [9.5 mm.].
*Average width.*—3/16" [4.8 mm.].
Skin:
*Thickness.*—Medium.
*Surface.*—Smooth.
*Tenacity.*—Tenacious to flesh.
*Astringency.*—Astringent.
*Tendency to crack.*—Somewhat in wet season.
*Color.*—Deep red [13. deep R] over a Deep reddish orange [36. deep rO] background with much Light orange yellow [70. l.OY] freckling toward the apex.
Flesh:
*Color.*—Brilliant yellow [83. brill.Y] from the stone to the skin, but will acquire a little Strong red [12. s.R] flecking next to the skin with further maturity.
*Surface of pit cavity.*—Light yellow [86. l.Y] broken fibers when twisted from stone.
*Amygdalin.*—Moderate.
*Juice.*—Moderate.
*Texture.*—Firm, crisp, melting.
*Fibers.*—Abundant, fine.
*Ripens.*—Earlier at the apex.
*Flavor.*—Acidic and sweet, typically 15 brix.
*Aroma.*—Moderate.
*Eating quality.*—Very good.

STONE

Type: Clingstone.
Form: Oval.
Hilum: Narrow.
Base: Straight, rounded.
Apex: Obtuse with a 1/16" [1.6 mm.] tip.
Sides: Slightly unequal.
Surface: Irregularly furrowed toward the apex, and pitted from base to above center.
Ridges: Rounded.
External color: Light yellowish brown [76. l.yBr].
Pit wall color when cracked: Light orange yellow [70. l.OY].
Cavity surface color: Pale orange yellow [73. p.OY].
Average pit wall thickness: 1/4" [6.4 mm.].
Average width: 1 1/4" [31.8 mm.].
Average length: 1 5/8" [41.3 mm.].
Average breadth: 7/8" [22.2 mm.].
Tendency to split: Slight.
Kernel:
*Form.*—Oval.
*Skin color.*—Pale yellow [89. p.Y] when first removed.
*Pellicle color.*—Moderate yellow [87. m.Y].
*Vein color.*—Light yellow [86. l.Y].
*Taste.*—Sweet.
*Viable.*—Yes.
*Average width.*—7/16" [11.1 mm.].
*Average length.*—7/8" [22.2 mm.].
*Amygdalin.*—Slight.

USE

Market: Fresh market and long distance shipping.
Keeping quality: Good, fruit quality observed to remain in good condition after 21 days in standard cold room at 36° Fahrenheit [2° Celsius].
Shipping quality: Good.
Resistance to insects: No unusual susceptibilities noted.
Resistance to diseases: No unusual susceptibilities noted.

OTHER NOTES

Although the new variety of nectarine tree possesses the described characteristics under the ecological conditions at Le Grand, Calif., in the central part of the San Joaquin Valley, it is to be expected that variations in these characteristics may occur when farmed in areas with different climatic conditions, different soil types, and/or varying cultural practices.

I claim:

1. A new and distinct variety of nectarine tree, substantially as illustrated and described, that is most similar to 'Rose Bright' (U.S. Plant Pat. No. 15,845) nectarine by producing nectarines that are very firm in texture, clingstone in type, yellow in flesh color, and full red in skin color, but is distinguished therefrom by requiring more chilling hours and by producing fruit that is larger in size, has more freckles on the apex, and matures about five days earlier.

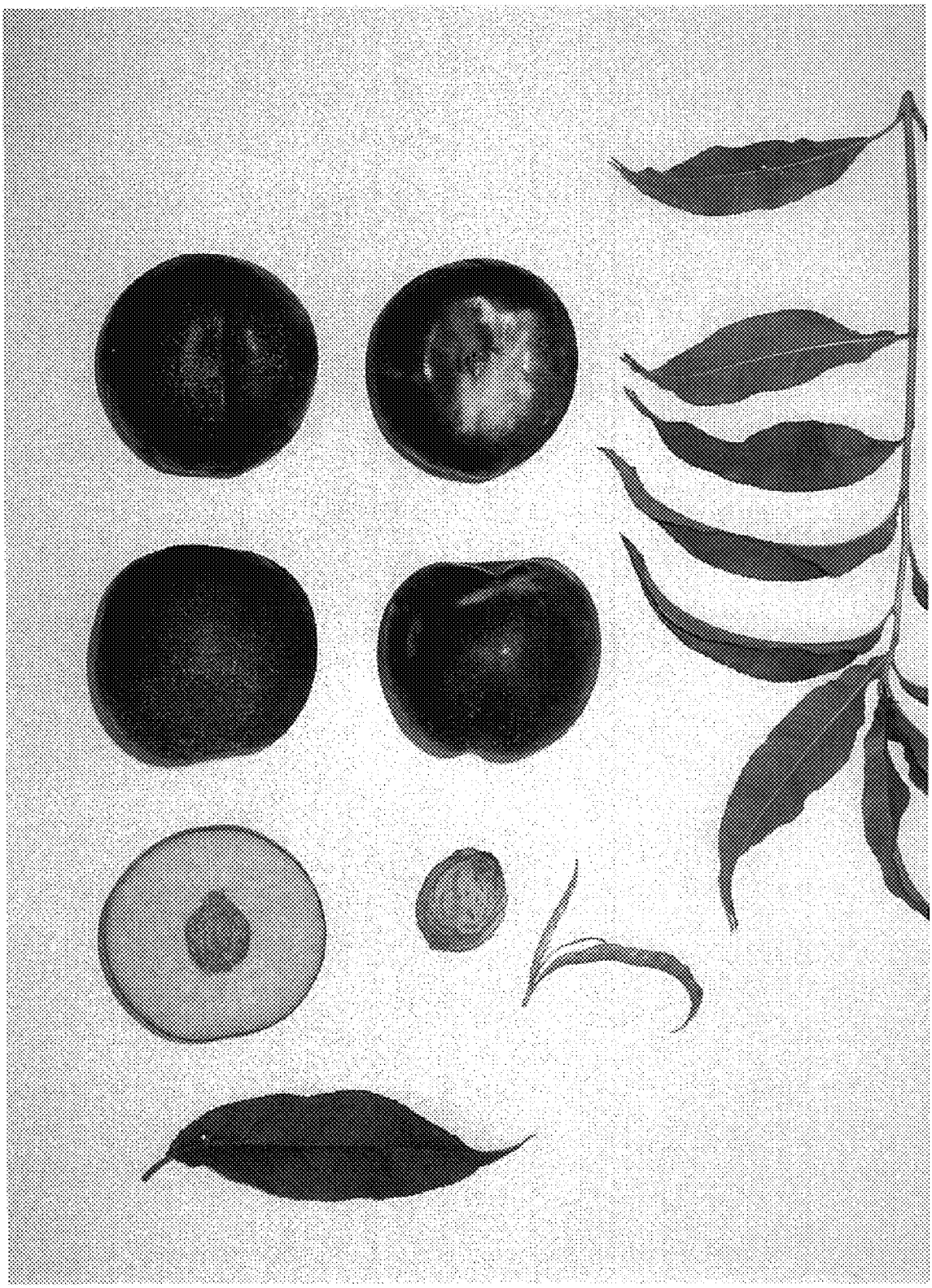

* * * * *